United States Patent
Bensch et al.

(10) Patent No.: US 7,218,397 B1
(45) Date of Patent: May 15, 2007

(54) METHODS AND SYSTEMS FOR COUNTING PARTICLES AND SENSING WATER

(75) Inventors: Leonard E. Bensch, Glen Cove, NY (US); Ian Reed, Hampshire (GB); Robert G. Simkins, Greenlawn, NY (US); William M. Needleman, Huntington, NY (US)

(73) Assignee: Pall Corporation, East Hills, NY (US)

( * ) Notice: Subject to any disclaimer, the term of this patent is extended or adjusted under 35 U.S.C. 154(b) by 251 days.

(21) Appl. No.: 10/088,175

(22) PCT Filed: Sep. 14, 2000

(86) PCT No.: PCT/US00/25092

§ 371 (c)(1),
(2), (4) Date: Dec. 13, 2002

(87) PCT Pub. No.: WO01/20323

PCT Pub. Date: Mar. 22, 2001

Related U.S. Application Data

(60) Provisional application No. 60/154,592, filed on Sep. 17, 1999.

(51) Int. Cl.
*G01N 15/02* (2006.01)

(52) U.S. Cl. .................. 356/335; 356/338; 356/73
(58) Field of Classification Search ........ 356/335–343, 356/70, 73, 432–440; 377/11–14
See application file for complete search history.

(56) References Cited

U.S. PATENT DOCUMENTS

| | | | |
|---|---|---|---|
| 2,552,088 A | 5/1951 | Davis | |
| 2,720,624 A | 10/1955 | Gunst et al. | |
| 3,238,452 A | 3/1966 | Schmitt et al. | |
| 3,320,428 A | 5/1967 | Wagstaffe et al. | |
| 3,357,236 A | 12/1967 | Kasten | |
| 3,522,530 A | 8/1970 | Muller | |
| 3,787,122 A * | 1/1974 | Lepper, Jr. | 356/338 |
| 4,013,953 A | 3/1977 | Skala | |
| 4,181,009 A | 1/1980 | Williamson | |
| 4,638,305 A | 1/1987 | Sutton | |
| 4,649,711 A * | 3/1987 | Sibley et al. | 62/129 |
| 5,089,780 A | 2/1992 | Megerle | |
| 5,118,959 A | 6/1992 | Caldow et al. | |
| 5,377,005 A * | 12/1994 | Meyer | 356/335 |
| 6,746,610 B2 * | 6/2004 | Manz et al. | 210/689 |

* cited by examiner

*Primary Examiner*—Hoa Q. Pham
(74) *Attorney, Agent, or Firm*—Leydig, Voit & Mayer, Ltd.

(57) ABSTRACT

A system (20) for sampling a non-aqueous liquid comprises an optical particle counter (1) and a water sensor (2).

32 Claims, 3 Drawing Sheets

METHODS AND SYSTEMS FOR COUNTING PARTICLES AND SENSING WATER

TECHNICAL FIELD

The present invention relates to methods and systems that improve the reliability of optical particle counters by assessing the presence and/or influence of water. More particularly, the present invention relates to methods and systems that optically count particulates present in non-aqueous liquids, such as oils, fuels, and other hydrocarbons, while accounting for the deleterious effect on accurate particle readings caused by the presence of water in the non-aqueous liquids.

BACKGROUND OF THE INVENTION

Non-aqueous liquids, particularly hydrocarbons such as transformer oils, motor oils, transmission fluids, and fuels may become contaminated with particulates during use. These contaminated liquids cause corrosion, wear, mechanical damage to and/or poor performance in the systems in which they are used. Accordingly, it is desirable to detect the presence and quantity of particulates present in these systems to determine when the liquid must be cleaned, processed or replaced.

Several methods exist for detecting particulates in liquids, including non-aqueous liquids. In one method, a sample is taken from the fluid path to a testing facility, mixed with a reagent and the quantity of particulates determined. This method is inefficient as it requires excess time and often leads to inaccurate results caused by contamination during transfer. In another method the liquid is redirected through a slipstream where the liquid is filtered for particulates. The quantity of particulates in the liquid may be inferred by sensing the change in the pressure drop across the filter. This method is reactionary and is ineffective in accurately counting the particulates present and maximizing utilization of the liquid.

In yet another method, a sample is taken, for example, in a slipstream, and the particulates are counted by an optical particle counter. This method is generally highly efficient, and, under the appropriate conditions, extremely accurate. However, counts from optical particle counters are dramatically influenced by the level of water present in a non-aqueous liquid. In many instances, erroneous counts are produced by the presence of water and the operator has no convenient, real time method to know that the counts are wrong. Some conventional solutions solved this problem by using methods, such as heating, to remove the water from the non-aqueous liquid to be tested so that a proper count could be achieved. However, this method may adversely affect the non-aqueous liquid and fails to address the combinatorial effect of water and particulate contamination on non-aqueous liquids.

SUMMARY OF THE INVENTION

According to one aspect of the invention, systems for sampling a non-aqueous liquid may include both an optical particle counter and a water sensor. The optical particle counter generates a signal indicative of the number of particles in the non-aqueous liquid, and the water sensor generates a signal indicative of the water content of the non-aqueous liquid.

According to another aspect of the present invention, methods for sampling a non-aqueous liquid may include directing a non-aqueous liquid into an optical particle counter and sensing the water content of the non-aqueous liquid.

Systems and methods embodying these aspects of the invention thus allow an operator to easily determine whether the particle count is suspect due to the water content of the non-aqueous liquid. If the water content reaches a level that may negatively influence the particle count, the operator knows that the particle count may be unreliable and he may take appropriate action.

According to another aspect of the present invention, methods for sampling a non-aqueous liquid may include sensing the water content of a non-aqueous liquid. The methods may further include directing the non-aqueous liquid to or away from an optical particle counter in response to the water content.

In systems and methods embodying this aspect of the invention, the non-aqueous liquid may be directed to the optical particle counter if the water content is below a value that can negatively influence the particle count. If the water content reaches a value where the optical counter will likely produce an erroneous result, the non-aqueous liquid may be redirected away from the optical particle counter. When the non-aqueous liquid is directed away from the optical particle counter, various embodiments provide for alternative particulate indicators, treatment units for decreasing the water content, and/or bypass lines.

DETAILED DESCRIPTION OF THE INVENTION

Counting particulates and sensing the water content of non-aqueous liquids, such as transformer oils, motor oils, transmission fluids, and fuels, may be accomplished by operatively coupling corresponding sensors to the non-aqueous liquid in a variety of locations. For example, the sensors may be operatively located directly in a main stream of the non-aqueous liquid or in a slipstream, e.g., a flow of the non-aqueous liquid through a secondary path. Using a slipstream for testing is generally preferable, although it is not required, so as to avoid affecting the main stream, for example, when sensors malfunction or require routine maintenance. Alternatively, the optical particle counter and/or the water sensor may be operatively coupled to the non-aqueous liquid in a reservoir or a container, such as a tank or bottle.

Figure 1:
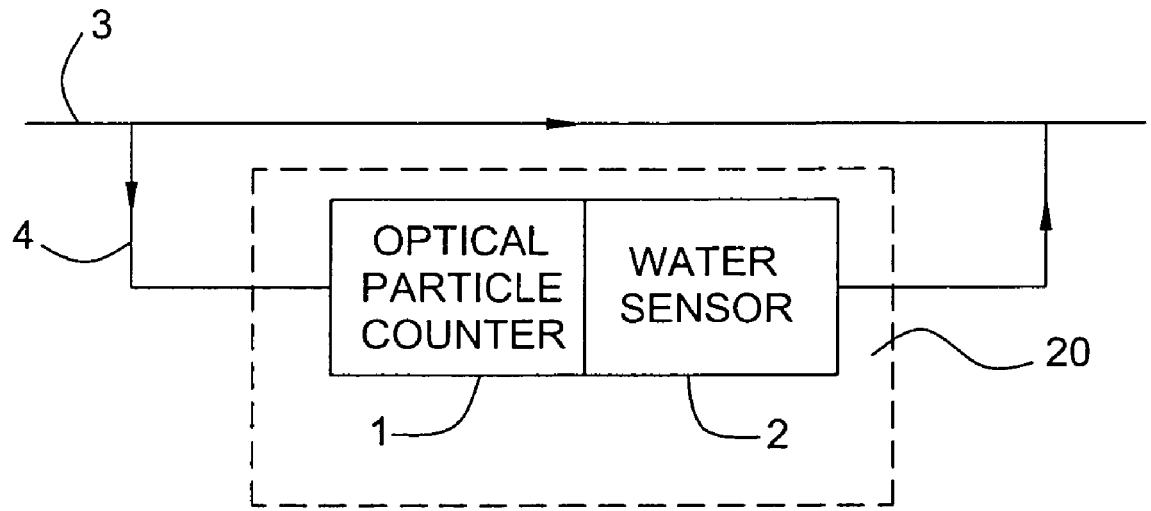
FIG. 1 illustrates a system for sampling a non-aqueous liquid.
Figure 2:
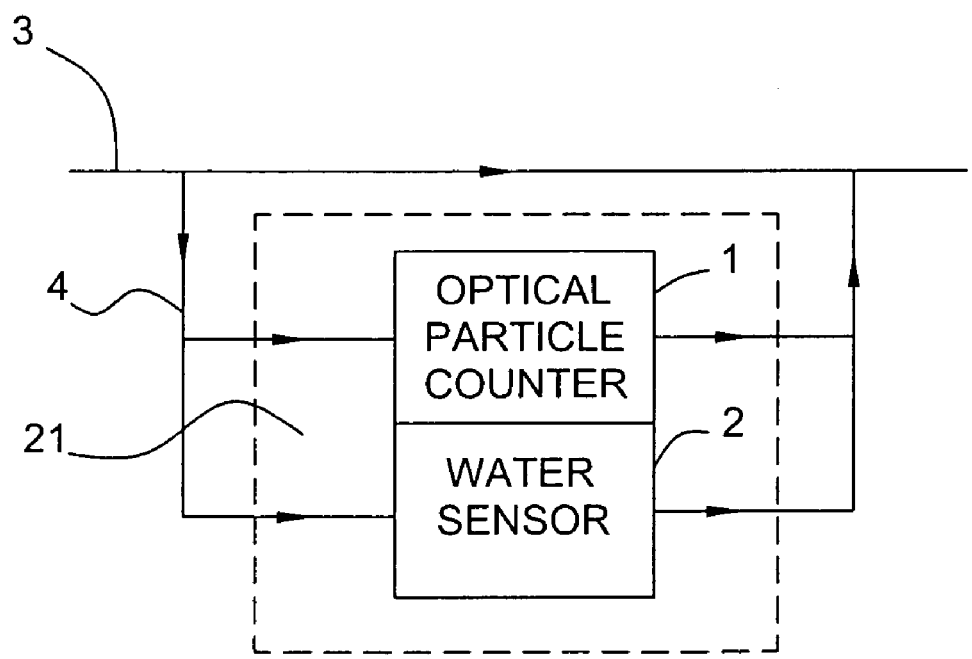
FIG. 2 illustrates another system for sampling a non-aqueous liquid.

Examples of systems for sampling a non-aqueous liquid, including counting particles and sensing water content, are illustrated in FIGS. 1 and 2. The sampling systems 20, 21 generally comprise an optical particle counter 1 and a water sensor 2, which may be disposed to sample the non-aqueous liquid in a slipstream 4 that is redirected away from and back toward a main stream 3. The optical particle counter 1 and the water sensor 2 may be operatively coupled to the non-aqueous liquid in series, with the optical particle counter 1 upstream, preferably closely upstream, of the water sensor 2, as shown in FIG. 1, or with the optical particle counter downstream, preferably closely downstream, of the water sensor. Alternatively, as shown in FIG. 2, the optical particle counter 1 and the water sensor 2 may be operatively coupled to the non-aqueous liquid in parallel. The water sensor 2 and the optical counter 1 are preferably placed sufficiently close in proximity that one of these components samples substantially similar portions of the non-aqueous liquid, e.g., the same portion of the non-aqueous liquid, soon after the other, as shown in FIG. 1, or at approximately the same time as the other, as in FIG. 2.

The optical particle counter 1 and the water sensor 2 may be implemented as separate components which sample the non-aqueous liquid separately, or they may be implemented as an integral unit which senses the number of particles and the water content in a sample of non-aqueous liquid at substantially the same time.

A wide variety of optical particle counters may be utilized with embodiments of the invention. Optical particle counters are preferred because of their accuracy and reliability in counting particulates present in a liquid. Many conventional optical particle counters comprise a chamber for testing a liquid, a light source that produces a beam of light that is received through a slit into the chamber and reflected through the liquid, and a measuring device for measuring the amount of obscuration or scattering caused in the beam of light. These and other optical systems provide particularly accurate counts under appropriate conditions. Optical particle counters are readily available from many companies, including Pacific Scientific, that make a full line of optical counters that count particulates with various degrees of accuracy.

Similarly, a wide variety of water sensors may be utilized with embodiments of the invention. For example, several water sensors are disclosed in International Publication No. WO 98/46984, entitled "Methods and Systems for Sensing Water in Liquids", assigned to Pall Corporation, and incorporated herein by reference. Water sensors may measure absolute water content, relative saturation water content or both. Water sensors may be implemented in a variety of ways. For example, many conventional water sensors measure the change in potential across a sample of non-aqueous liquid caused by the increase in conductivity due to the presence of water. Water sensors may also include temperature sensors to account for changes in the water content with temperature variations. Water sensors are readily available from many companies, including Vaisala Company and Pall Corporation.

In a preferred mode of operation, a portion of the non-aqueous liquid flowing in the main stream 3 may be directed into the slipstream 4, past the optical particle counter 1 and the water sensor 2, and back to the main stream 3. The non-aqueous liquid may be directed past the optical particle counter before, after or at substantially the same time that the non-aqueous liquid is directed past the water sensor, depending, for example, on whether the optical particle counter is upstream, downstream, in parallel with, or integrated with the water sensor. As the non-aqueous liquid flows past the optical particle counter 1, it generates a signal indicative of the number of particles in the non-aqueous liquid. As the non-aqueous liquid flows past the water sensor, it generates a signal indicative of the water content of the non-aqueous liquid.

The optical particle counter 1 and the water sensor 2 may each comprise a processing circuit and a display that receive the various signals produced by their corresponding counting or sensing implementation and produce a visual indication indicative of the results, which may then be interpreted by an operator. The visual indication may be a readout of the particle count or the water content. The water sensor may provide a different visual indication, e.g., one which simply indicates one or more water content ranges. With the water sensor 2 and the optical particle counter 1 sufficiently close, the operator may conveniently and reliably utilize the visual indication of the water sensor to determine the implications of the water content on the particle count. The water sensor thus provides a reliability indicator to determine if the optical particle counter is producing a reliable result due to the presence of water in the non-aqueous liquid. For many non-aqueous liquids, a higher water content may indicate a less reliable particle count.

Figure 3:
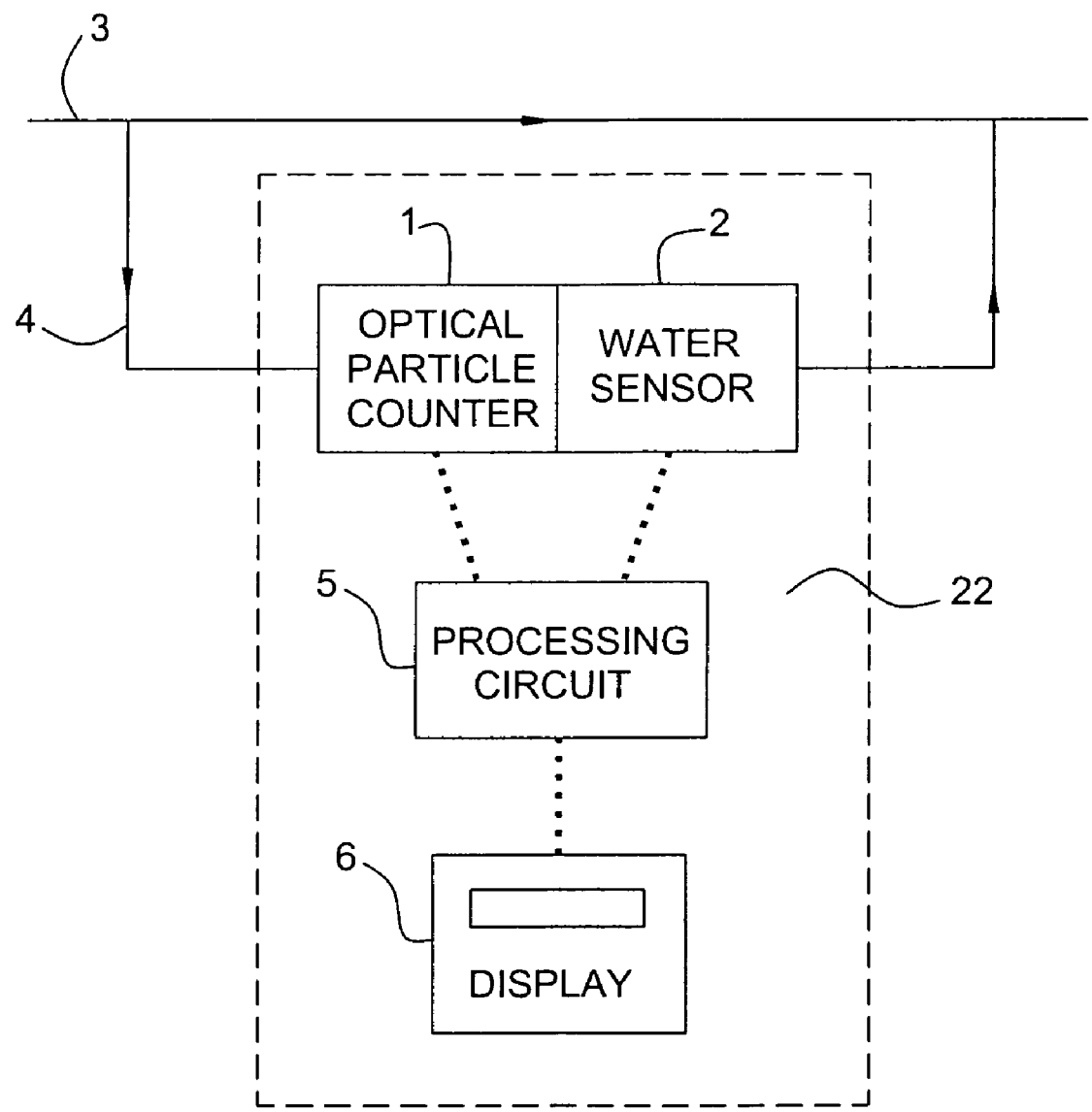
FIG. 3 illustrates another system for sampling a non-aqueous liquid.

Another example of a system for sampling a non-aqueous liquid is shown in FIG. 3. The system 22 includes an optical particle counter 1 and a water sensor 2 disposed in a slipstream 4 of a main stream 3 with the optical particle counter 1 upstream of the water sensor 2. However, the optical particle counter and the water sensor may be operatively coupled to the non-aqueous liquid in any other suitable manner, as previously described. For example, the optical particle counter and the water sensor may be disposed in the main stream, may be disposed in series with the water sensor upstream of the optical particle counter, may be disposed in parallel or may be integrated with one another.

The sampling system 22 may further include a processing circuit 5 and a display 6. The processing circuit 5 may be coupled to at least one of and preferably both of the optical particle counter 1 and the water sensor 2. The display 6 may be coupled to at least one of the optical particle counter 1, the water sensor 2, and the processing circuit 5, preferably at least the processing circuit 5. In the illustrated embodiment, the processing circuit 5 is shown as a separate component and it may be implemented in any suitable manner, e.g., as a general purpose computer, a microprocessor, a logic array, or any other suitable processing circuitry. Similarly, the display 6 is shown as a separate component, and it may be implemented in any suitable manner, e.g., as a CRT or a flat panel display and/or one or more lightable indicators. However, the processing circuit or the display or both may be integral components of one another, the optical particle counter and/or the water sensor. For example, the processing circuit and the display may be implemented as a computer with a flat panel or CRT display and the computer may be connected to an integral unit comprising the optical particle counter and the water sensor. Regardless of how the processing circuit is implemented, the processing circuit may store data received from the optical particle counter and/or the water sensor so it may be viewed immediately or at a later time by the operator. The processing circuit may also download the data to other processing circuits, e.g., computers for further display or analysis.

In a preferred mode of operation, a portion of the non-aqueous liquid may be directed from the main stream 3 into the slipstream 4, past the optical particle counter 1 and the water sensor. 2, and back to the main stream 3, as previously described. As the non-aqueous liquid flows past the optical particle counter 1 and the water sensor 2, they respectively generate a signal indicative of the number of particles in the non-aqueous liquid and a signal indicative of the water content of the non-aqueous liquid.

The processing circuit 5 may respond to the signals input from the optical particle counter 1 and/or water sensor 2 in a variety of ways. For example, the processing circuit 5 may receive a signal indicating water content from the water sensor 2 and a signal indicating the particle count from the optical particle counter 1 and then simply generate display signals. The display signals may be transferred to the display 6 and result in a readout of the particle count as determined by the optical particle counter 1 and a visual indication of the water content, e.g., a readout of the water content, as determined by the water sensor 2. As disclosed with respect to the embodiments shown in FIGS. 1 and 2, the water content indication of the water sensor provides a reliability indicator for the particle count. If the reliability indicator indicates that the particle count is sufficiently unreliable, the operator may simple ignore the count.

Alternatively, the processing circuit 5 may include one or more subcircuits for further processing signals input from the optical particle counter 1 and/or the water sensor 2. For example, the processing circuit 5 may include a threshold subcircuit which may store one or more threshold values. Each threshold value may correspond to a water content in a given non-aqueous liquid which calls into question a particle count produced by the optical particle counter 1. For example, for a given non-aqueous liquid the particle count may be substantially accurate below a first predetermined water content value, e.g., below a relative saturation value of, say, up to 90% or more; may be somewhat inaccurate between the first predetermined water content value and a second predetermined water content value, e.g., between relative saturation values of, say, 90% and up to about 100% or more; and may be substantially inaccurate above the second predetermined water content value, e.g., above the relative saturation value of 100%. Values of 90% and 100% for the first and second predetermined water content values, respectively, are merely exemplary. Each predetermined water content value may vary depending on factors such as the nature of the non-aqueous liquid and the type of optical particle counter and may be determined empirically.

The threshold subcircuit may store the predetermined value(s), e.g., the first and second predetermined values, as the threshold values and may compare them to the water content signal received from the water sensor. The threshold subcircuit may be configured in any suitable manner for storing the threshold value(s) and performing the comparison. For example, the threshold subcircuit may be implemented as a memory containing a threshold lookup table, a comparator for comparing the water content signal with the stored threshold values, and control logic for determining a course of action based on the comparison results. The processing circuit 5 may then generate a display signal indicative of the number of particles in the non-aqueous liquid and one or more display signals in accordance with the output of the threshold subcircuit.

The display 6 may be configured in a variety of ways to provide an indication of the particle count and an indication of the water content as a reliability indicator for the displayed particle count. For example, the display 6 may include several lightable indicators, e.g., green, yellow, and red lamps, in addition to a particle count readout. Depending on the output of the threshold subcircuit and, in turn, the display signals generated by the processing circuit 5: (1) the green lamp may be lit if the water content is in a first reliability range, i.e., below the first threshold value, signalling the operator that the displayed particle count is likely to be substantially accurate; (2) the yellow lamp may be lit if the water content is in a second reliability range, i.e., between the first and second threshold values, signalling the operator that the displayed particle count is likely to somewhat inaccurate; and (3) the red lamp may be lit if the water content is in a third reliability range, i.e., above the second threshold value, signalling the operator that the displayed particle count is likely to be substantially inaccurate. While the threshold subcircuit and the display have been described in terms of two threshold values and three reliability ranges, more or fewer threshold values and reliability ranges may be provided. Further, while the reliability ranges have been implemented in the display by lightable indicators such as lamps, other visual indications and/or audible indications, such as alarms, may be used.

In yet another alternative, the processing circuit may include circuitry which adjusts the indication of the particle count input from the particle counter 1 in accordance with the indication of the water content input from the water sensor 2. For example, the water content in a given non-aqueous liquid may falsely increase, or decrease, the particle count sensed by the optical particle counter 1. The relationship between the water content and the excess counts, or the count shortfall, may be empirically determined for the non-aqueous liquid and implemented in the processing circuit 5, e.g., in an adjustment subcircuit. This implementation may be configured in a variety of ways, including a lookup table or a logic array. In any event, the adjustment subcircuit may operate on the signal input from the optical particle counter 1 in accordance with the signal input from the water sensor 2 to provide an adjusted indication of the particle count which more accurately represents the true particle count. The processing circuit 5 may then generate a display signal in accordance with an adjusted particle count signal and transfer the display signal to the display 6. The display 6 may then provide a readout of the adjusted particle count. The display 6 may also provide a reliability indication such as a readout of the water content or a visual indication of the reliability range. However, because the processing circuit 5 has adjusted the sensed particle count in accordance with the sensed water content to provide an adjusted, more accurate particle count, a reliability indicator may not be included with the display 6.

Figure 4:
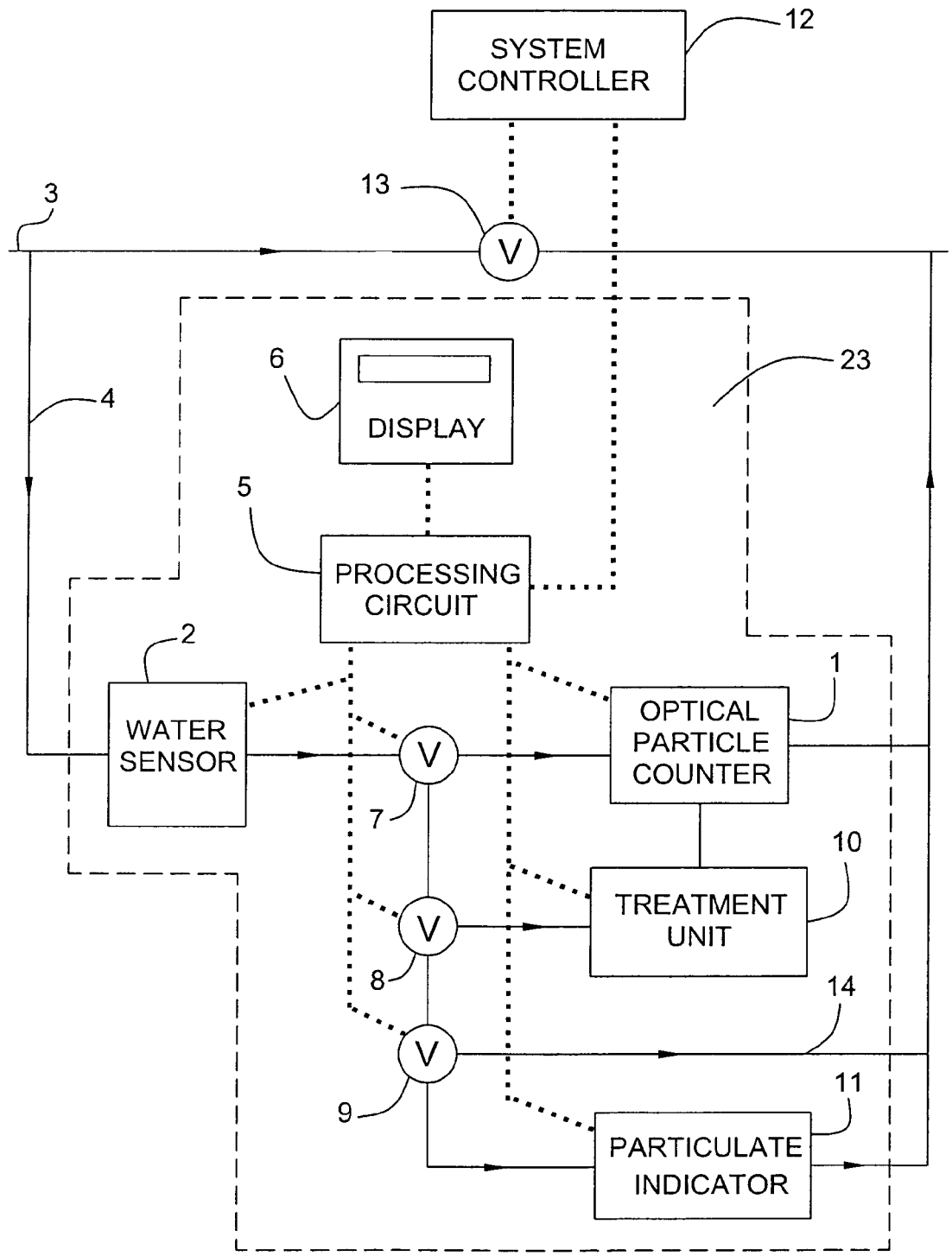
FIG. 4 illustrates another system for sampling a non-aqueous liquid.

Another example of a system for sampling a non-aqueous liquid is shown in FIG. 4. The sampling system 23 includes an optical particle counter 1, a water sensor 2, and a display 6 coupled to a processing circuit 5, as shown in FIG. 3. The optical particle counter 1 and the water sensor 2 are disposed in a slipstream 4 of a main stream 3 with the optical particle counter 1 downstream of the water sensor 2. However, the components of this system may be implemented in other suitable configurations and disposed in the non-aqueous liquid in any other suitable manner, such as those previously described with respect to the embodiments of FIGS. 1–3. For example, the optical particle counter and the water sensor may be disposed in the main stream, may be disposed in series with the water sensor downstream of the optical particle counter, or may be disposed in parallel. However, in this embodiment, the optical particle counter and the water sensor are preferably not located at the same point in the non-aqueous liquid stream.

The sampling system further includes a valve arrangement coupled to the processing circuit 5. The valve arrangement may be implemented in a wide variety of ways. In the illustrated embodiment, the valve arrangement comprises first, second, and third valves 7, 8, 9, each coupled to the processing circuit 5. The valve arrangement allows the non-aqueous liquid to be directed to the optical particle counter 1 or away from the optical particle counter 1 in accordance with the water content sensed by the water sensor 2. For example, the processing circuit 5 may receive a water content signal input from the water sensor 2 and determine if the water content is within or outside of a range in which the optical particle counter 1 provides a reliable, accurate particle count. This function may be implemented, for example, in a threshold subcircuit similar to the threshold subcircuit previously described. If the water content is within the range, the processing circuit 5 may generate a valve control signal which operates the first valve 7 to direct the non-aqueous liquid from the water sensor 2 into the optical particle counter 1. A readout of the particle count and a reliability indicator may then be displayed on the display 6. If the water content is outside of the range in which the optical particle counter 1 provides a reliable, accurate particle count, the processing circuit 5 may generate a valve control signal which operates the first valve 7 to direct the non-aqueous liquid away from the optical particle counter 1.

When the non-aqueous liquid is directed away from the optical particle counter 1, it may be directed along a wide variety of suitable alternative flow paths. For example, the sampling system may include a treatment unit 10 which operates to decrease the water content in the non-aqueous liquid. The treatment unit may be implemented in a wide variety of suitable ways, including as a coalescing and/or separating assembly or a heater. The processing circuit 5 may generate a valve control signal which operates the second valve 6 to direct non-aqueous liquid into the treatment unit 10. Once the water content of the non-aqueous liquid has been decreased, the non-aqueous liquid may be directed back to the optical particle counter 1 to obtain a more accurate particle count. The non-aqueous liquid may pass directly from an output of the treatment unit 10 to the optical particle counter 1. The optical particle counter 1 may then provide a signal indicative of a particle count to the processing circuit 5 which then may be displayed on the display 6. However, because the particle count sensed by the optical particle counter 1 is biased on a non-aqueous liquid having a lower water content than that sensed by the water sensor 2, the reliability indicator shown on the display 6 may be disabled. Alternatively, a second water sensor (not shown) may be operatively coupled to the non-aqueous liquid flow path between the treatment unit and the optical particle counter and may be coupled to the processing circuit. Consequently, when the processing circuit directs the non-aqueous liquid through the treatment unit, past the second water sensor, and to the optical particle counter, it may display the count indicated by the optical particle counter and the water content indicated by the second water sensor.

Alternatively, or additionally, when the non-aqueous liquid is directed away from the optical particle counter 1, it may simply be directed to a bypass line which returns the non-aqueous liquid to the main stream 4. For example, the processing circuit 5 may generate valve control signals which operate the second and third valves 8, 9 to direct the non-aqueous liquid through a bypass line 14 coupled to the slipstream 4 and hence the main stream 3. The processing circuit 5 and the display 6 may be configured in any suitable manner which provides an indication that the optical particle counter is being bypassed.

As yet another alternative, or addition, when the non-aqueous liquid is directed away from the optical particle counter it may be directed to another particulate indicator 11, for example, any particulate indicator other than an optical particle counter which is less sensitive to water content. Preferably, the particulate indicator 11 includes a porous medium, such as a porous mesh, through which the non-aqueous liquid flows. A fluid flow characteristic, such as differential pressure across the porous medium, is sensed to provide an indication of the quantity of particulates in the non-aqueous liquid. The particulate indicator 11 may generate a signal indicative of the quantity of particulates sensed and the signal may be provided to the processing circuit 5. The processing circuit 5, in turn, may display the particulate indication on the display 6, with or without the reliability indicator. From the particulate indicator 11, the non-aqueous liquid may be returned to the main stream 3.

The sampling system 23 shown in FIG. 4 may operate independently of any main system controller or it may operate in conjunction with a main system controller. For example, the processing circuit 5 may be coupled to a system controller 12 to provide a variety of data and instructions between them. For example, the processing circuit 5 may relay the water content signal provided by the water sensor 2, the particle count signal generated by the optical particle counter 1, and/or the particulate signal generated by the particulate indicator 11 to the system controller 12. Depending on the value of the signals, the system controller 12 may then control the main system in a variety of ways. For example, if the water content or the particulate content as indicated by the water sensor 2, the optical particle counter 1 or the particulate indicator 11 is unusually high, the system controller may shut off the main stream 3, e.g., by operating a main valve 13 accordingly.

Various aspects of the invention have been described with respect to many embodiments. However, the invention is not limited to these embodiments. For example, one or more of the features of any of these embodiments may be combined with one or more of the features of the other embodiments without departing from the scope of the invention. Further, one or more of the features of any of these embodiments may be modified or omitted without departing from the scope of the invention. Accordingly, the various aspects of the invention include any and all methods and systems encompassed within the spirit and scope of the invention as defined by the following claims.

What is claimed is:

1. A system for sampling a non-aqueous liquid comprising:
 a water sensor capable of being coupled to a non-aqueous liquid to sense an indication of the water content of the non-aqueous liquid;
 an optical particle counter capable of being coupled to the non-aqueous liquid to provide an indication of the number of particulates present in the non-aqueous liquid; and
 a processing circuit operatively coupled to at least one of the water sensor and the optical particle counter, wherein the processing circuit signals implications of the water content on the particle count.

2. The system of claim 1 wherein the water sensor and the optical particle counter are disposed in a slipstream of the non-aqueous liquid.

3. The system of claim 1 wherein the water sensor is disposed downstream of the optical particle counter.

4. The system of claim 1 wherein the water sensor is disposed upstream of the optical particle counter.

5. The system of claim 1 wherein the water sensor and the optical particle counter are disposed in parallel in the non-aqueous liquid.

6. The system of claim 1 wherein the water sensor generates a signal indicative of relative saturation water content.

7. The system of claim 1 wherein the water sensor generates a signal indicative of absolute water content.

8. The system of claim 1 wherein the optical particle counter generates a signal indicative of the number of particles in the non-aqueous liquid.

9. The system of claim 1 wherein the processing circuit receives a signal indicative of the water content from the water sensor.

10. The system of claim 1 wherein the processing circuit receives a signal indicative of the particle count from the optical particle counter.

11. The system of claim 1 wherein the processing circuit signals implications of the water content on the particle count in accordance with one or more threshold values related to the water content.

12. The system of claim 1 wherein the processing circuit provides an indication of the particle count and an indication of the reliability of the particle count in accordance with the water content.

13. The system of claim 12 wherein the processing circuit provides an indication of the reliability of the particle count in accordance with one or more threshold values related to the water content.

14. The system of claim 1 further comprising a valve arrangement coupled to the processing circuit.

15. The system of claim 1 wherein the water sensor and the optical particle counter comprise an integral unit.

16. A system for sampling a non-aqueous liquid comprising:
   a water sensor capable of being coupled to a non-aqueous liquid to sense an indication of the water content of the non-aqueous liquid;
   an optical particle counter capable of being coupled to the non-aqueous liquid to provide an indication of the number of particulates present in the non-aqueous liquid;
   a processing circuit operatively coupled to at least one of the water sensor and the optical particle counter; and
   a valve arrangement coupled to the processing circuit, wherein the processing circuit and the valve arrangement are arranged to direct non-aqueous liquid away from the optical particle counter in accordance with the signal indicative of the water content.

17. The system of claim 16 further comprising a treatment unit coupled to the valve arrangement and arranged to decrease the water content in the non-aqueous liquid.

18. The system of claim 17 wherein the treatment unit includes an outlet coupled to the optical particle counter.

19. A system for sampling a non-aqueous liquid comprising:
   a water sensor capable of being coupled to a non-aqueous liquid to sense an indication of the water content of the non-aqueous liquid;
   an optical particle counter capable of being coupled to the non-aqueous liquid to provide and indication of the number of particulates in the non-aqueous liquid;
   a processing circuit operatively coupled to at least one of the water sensor and the optical particle counter;
   a valve arrangement coupled to the processing circuit; and
   a bypass line coupled to the valve arrangement and arranged to bypass the optical particle counter.

20. A method for sampling a non-aqueous liquid comprising:
   directing the non-aqueous liquid into an optical particle counter and generating a signal indicative of the number of particles present in the non-aqueous liquid;
   sensing the water content of the non-aqueous liquid; and
   providing an indication of the reliability of the number of particles counted by the optical particle counter in accordance with the sensed water content.

21. The method of claim 20 wherein the non-aqueous liquid is directed into the optical particle counter after sensing the water content of the non-aqueous liquid.

22. The method of claim 20 wherein the non-aqueous liquid is directed into the optical particle counter before sensing the water content of the non-aqueous liquid.

23. The method of claim 20 wherein the non-aqueous liquid is directed into the optical particle counter at substantially the same time as sensing the water content of the non-aqueous liquid.

24. A method for sampling a non-aqueous liquid comprising:
   sensing an indication of the water content of the non-aqueous liquid; and
   in response to the water content indication either (1) directing the non-aqueous liquid into an optical particle counter and generating a signal indicative of the number of particles in the non-aqueous liquid or (2) directing the non-aqueous liquid away from the optical particle counter.

25. The method of any of claim 24 wherein directing the non-aqueous liquid away from the optical particle counter includes directing the non-aqueous liquid into a treatment unit which decreases the water content of the non-aqueous liquid.

26. The method of claim 25 further comprising directing the non-aqueous liquid from the treatment unit into an optical particle counter.

27. The method of claim 24 wherein directing the non-aqueous liquid away from the optical particle counter includes bypassing the optical particle counter.

28. The method of claim 24 wherein directing the non-aqueous liquid away from the optical particle counter includes directing the non-aqueous liquid into a particulate indicator.

29. The method of claim 28 wherein directing the non-aqueous liquid into a particulate indicator includes passing the non-aqueous liquid through a porous medium and sensing a characteristic of non-aqueous liquid flow through the porous medium.

30. The method of claim 29 wherein sensing a characteristic of non-aqueous liquid flow through the porous medium includes sensing the pressure differential across the porous medium.

31. The method of claim 24 wherein sensing an indication of the water content includes sensing an indication of the relative saturation water content of the non-aqueous liquid.

32. The method of claim 24 wherein sensing an indication of the water content includes sensing an indication of the absolute water content of the non-aqueous liquid.

* * * * *